(12) United States Patent
Kriegel et al.

(10) Patent No.: US 12,077,556 B2
(45) Date of Patent: Sep. 3, 2024

(54) PROCESS FOR PREPARING CONCENTRATED SOLUTIONS OF STEVIOL GLYCOSIDES, AND USES

(71) Applicant: The Coca-Cola Company, Atlanta, GA (US)

(72) Inventors: Robert M. Kriegel, Decatur, GA (US); Indra Prakash, Alpharetta, GA (US)

(73) Assignee: The Coca-Cola Company, Atlanta, GA (US)

( * ) Notice: Subject to any disclaimer, the term of this patent is extended or adjusted under 35 U.S.C. 154(b) by 771 days.

(21) Appl. No.: 17/056,283

(22) PCT Filed: May 17, 2019

(86) PCT No.: PCT/US2019/032827
§ 371 (c)(1),
(2) Date: Nov. 17, 2020

(87) PCT Pub. No.: WO2019/222601
PCT Pub. Date: Nov. 21, 2019

(65) Prior Publication Data
US 2021/0115081 A1    Apr. 22, 2021

Related U.S. Application Data

(60) Provisional application No. 62/672,799, filed on May 17, 2018.

(51) Int. Cl.
*C07H 15/256*    (2006.01)
*A23L 2/60*    (2006.01)
*A23L 27/30*    (2016.01)
*C07H 1/00*    (2006.01)

(52) U.S. Cl.
CPC .............. *C07H 15/256* (2013.01); *A23L 2/60* (2013.01); *A23L 27/36* (2016.08); *C07H 1/00* (2013.01)

(58) Field of Classification Search
CPC ......... C07H 15/256; C07H 1/00; A23L 27/36; A23L 2/60
See application file for complete search history.

(56) References Cited

U.S. PATENT DOCUMENTS

| | | |
|---|---|---|
| 2014/0171519 A1 | 6/2014 | Prakash et al. |
| 2014/0357588 A1 | 12/2014 | Markosyan et al. |
| 2015/0017284 A1 | 1/2015 | Prakash et al. |

FOREIGN PATENT DOCUMENTS

| | | |
|---|---|---|
| CN | 106866757 | 6/2017 |

OTHER PUBLICATIONS

International Search Report for PCT/US2019/032827, issued Sep. 9, 2019.
Prakash, I. et al., "Development of Next Generation Stevia Sweetener: Rebaudioside M", Foods, 2014, vol. 3, pp. 162-175.

*Primary Examiner* — Leigh C Maier
(74) *Attorney, Agent, or Firm* — King & Spalding

(57) ABSTRACT

Methods of preparing concentrated solutions of crystalline steviol glycoside compositions having relatively high rebaudioside M content are provided herein. The concentrated solutions are stable and can be used to prepared beverage syrups and, ultimately, beverages. Methods of preparing beverage syrups and beverages are also detailed herein.

17 Claims, No Drawings

PROCESS FOR PREPARING CONCENTRATED SOLUTIONS OF STEVIOL GLYCOSIDES, AND USES

CROSS REFERENCE TO RELATED APPLICATIONS

This application is a national phase application under 35 U.S.C. § 371 of International Application No. PCT/US2019/032827, filed May 17, 2019, which claims priority to U.S. Provisional Application No. 62/672,799, filed May 17, 2018. The contents of each of the above-identified applications is hereby fully incorporated herein by reference.

FIELD OF THE INVENTION

The present invention relates generally to methods of preparing beverage concentrates from crystalline steviol glycosides compositions containing relatively high rebaudioside M content for use in preparing beverage syrups and ultimately, beverages. Methods of preparing beverage syrups and beverages from the concentrated solutions are also provided herein.

BACKGROUND OF THE INVENTION

*Stevia* is the common name for *Stevia rebaudiana* (Bertoni), a perennial shrub of the Asteracae (Compositae) family native to Brazil and Paraguay. *Stevia* leaves, the aqueous extract of the leaves, and purified steviol glycosides isolated from *Stevia* have been developed as sweeteners desirable as both non-caloric and natural in origin. Steviol glycosides isolated from *Stevia rebaudiana* include stevioside, rebaudioside A, rebaudioside C, dulcoside A, rubusoside, steviolbioside, rebaudioside B, rebaudioside D and rebaudioside F.

Rebaudioside M (also called rebaudioside X), (13-[(2-O-β-D-glucopyranosyl-3-O-β-D-glucopyranosyl-β-D-glucopyranosyl)oxy] ent kaur-16-en-19-oic acid-[(2-O-β-D-glucopyranosyl-3-O-β-D-glucopyranosyl-β-D-glucopyranosyl) ester], was isolated from *Stevia rebaudiana* and characterized:

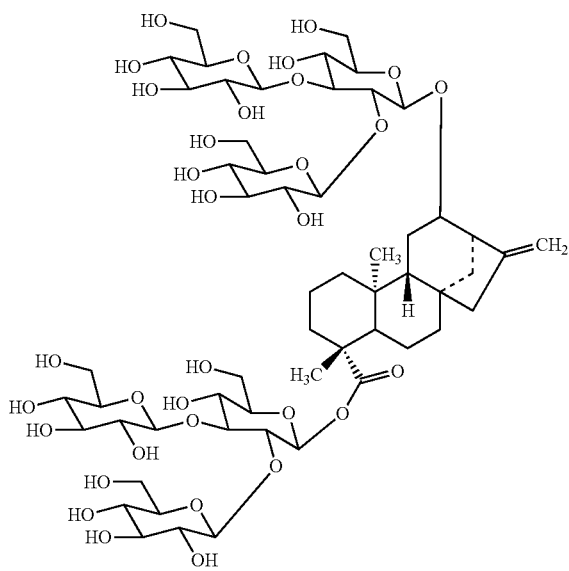

Many steviol glycosides are present in minute quantities in *Stevia rebaudiana*, including rebaudioside M which represents only about 0.050%-0.% by weight of the leaf. Recently, it was found that rebaudioside M could be used as a sweetener for beverages.

A concentration of at least about 0.300 (00 w/w) is useful in syrup and beverage formulations. However, crystalline rebaudioside M compositions have poor aqueous solubility and dissolution qualities in beverage formulations. For example, certain crystalline compositions containing about 75-90 rebaudioside M and about 25-10% rebaudioside D by weight cannot be dissolved above concentrations of 0.1-0.15% (% w/w) at room temperature.

Increasing the temperature of the solution can increase the solubility, as can the addition of co-solvents such as ethanol. However, these are not desirable approaches compatible with the syrup manufacture process.

Previous methods of improving the solubility of Reb M focused on spray-drying, i.e. they involved an amorphous or disordered crystalline form, whereas it is a crystalline form (e.g. Form A, WO2014098833) that is typically obtained via purification of *Stevia* leaf.

As such, there remains a need for methods to improve the dissolution properties of crystalline compositions containing relatively high rebaudioside M content, thereby providing concentrated solutions useful for, e.g., preparing beverage syrups.

SUMMARY OF THE INVENTION

The present invention generally relates to methods of preparing concentrated solutions having dissolved rebaudioside M content comprising:
  a. combining (i) a crystalline composition comprising rebaudioside M, (ii) at least one surfactant selected from a cationic surfactant and an anionic surfactant and (iii) an aqueous solution to provide a mixture;
  b. heating the mixture to provide a clear solution; and
  c. cooling the clear solution to provide a concentrate.

The method provides concentrates which are clear by visual inspection and have at least about 0.3 wt % steviol glycoside content, more preferably about 3 wt % or more steviol glycoside content.

The crystalline composition comprising rebaudioside M is preferably a steviol glycoside composition. In one embodiment, the crystalline steviol glycoside composition comprises at least about 80% rebaudioside M by weight. In another particular embodiment, the crystalline steviol glycoside composition comprises at least about 95% rebaudioside M by weight.

In one embodiment, the weight ratio of the crystalline steviol glycoside composition to at least one surfactant is from about 20:1 to about 1:20.

The concentrates can then be used in beverage syrup preparation, e.g. by combining the concentrate with additional sweeteners, functional ingredients, additives and combinations thereof.

The beverage syrups can then be used to prepare ready-to-drink beverages, e.g. carbonated beverages. Ready-to-drink beverages are prepared by mixing the beverage syrup with a quantity of diluting water.

DETAILED DESCRIPTION OF THE INVENTION

The present invention generally relates to methods of preparing concentrated solutions from crystalline compositions containing relatively high rebaudioside M content, which can be used to form beverage syrups and, ultimately, beverages.

I. Definitions

"Beverage", as used herein, refers to liquids suitable for human consumption.

"Solution", as used herein, refers to a liquid mixture in which the minor component (the solute) is uniformly distributed within the major component (the solvent). A solution is clear and does not contain particulate matter or precipitates, in contrast to a suspension.

"Syrup" or "Beverage syrup", as used herein, refers to a beverage precursor to which a fluid, typically water, is added to form a ready-to-drink beverage, or a "beverage." Typically, the volumetric ratio of syrup to water is between 1:3 to 1:8, more typically between 1:4 and 1:5. The volumetric ratio of syrup to water also is expressed as a "throw." A 1:5 ratio, which is a ratio commonly used within the beverage industry, is known as a "1+5 throw."

"Total steviol glycoside content", as used herein, refers to the sum of the relative weight contributions of each steviol glycoside in a sample.

II. Methods of Preparing Concentrates

In one embodiment, a method of preparing a concentrate from a crystalline composition comprising rebaudioside M comprises (a) combining (i) a crystalline steviol glycoside composition comprising rebaudioside M, (ii) at least one ionic surfactant and (iii) an aqueous solution to provide a mixture, (b) heating the mixture to provide a clear solution; and (c) cooling the clear solution to provide a concentrate.

The aqueous solution is typically water or an aqueous buffer. The water can be any typical water used to manufacture beverages, e.g. deionized water, distilled water, reverse osmosis water, carbon-treated water, purified water, demineralized water and combinations thereof.

The amount of aqueous solvent used can vary but corresponds to the amount necessary to achieve the desired concentrate concentration, i.e. wt %.

The method of the present invention is particularly useful for preparing concentrates having at least about 0.3 wt % steviol glycoside content, such as, for example, about 0.5% or greater, about 1% or greater, about 2% or greater, about 3% or greater, about 4% or greater, about 5 wt % or greater, about 10 wt % or greater, about 15 wt % or greater, about 20 wt % or greater, about 25 wt % or greater, about 30 wt % or greater or about 35 wt % or greater.

The method is also useful for preparing concentrates having at least about 0.3 wt % rebaudioside M content, such as, for example, about 0.5% or greater, about 1% or greater, about 2% or greater, about 3% or greater, about 4% or greater, about 5 wt % or greater, about 10 wt % or greater, about 15 wt % or greater, about 20 wt % or greater, about 25 wt % or greater, about 30 wt % or greater or about 35 wt % or greater.

Suitable buffers are any typical beverage buffer, e.g. citrate buffer or phosphate buffer.

The pH of the concentrate can be from about 2 to about 9, such as, for example, from about 2 to about 5.

Ionic surfactants include anionic and cationic surfactants. One or more ionic surfactants can be used in the methods and compositions herein.

Anionic surfactants include, but are not limited to, sulfates, sulfonates, phosphate esters and carboxylates. Exemplary sulfates include ammonium laurel sulfate, sodium dodecylbenzenesulfonate, sodium dodecyl sulfate (SDS), sodium laureth sulfate (SLS), sodium myreth sulfate, dioctyl sodium sulfosuccinate (DOSS), linear alkyl benzene sulfonates and sodium dodecyl sulfate (SDS). Exemplary carboxylates include alkyl carboxylates (soaps), such as sodium stearate. Other anionic surfactants include sodium cholate, sodium glycocholate, sodium taurodeoxycholate and sodium stearoyl lactylate.

Exemplary cationic surfactants include octenidine dihydrochloride, cetyl trimethylammonium bromide (CTAB), cetylpyridinium chloride, benzalkonium chloride, benzethonium chloride, 5-bromo-5-nitro-1,3-dioxane, dimethyldioctadecylammonium chloride, choline chloride, cetrimonium bromide, hexadecyltrimethylammonium bromide and dioctdecyldimethylammoniumbromide.

In one embodiment, the at least one ionic surfactant comprises sodium dodecyl sulfate (SDS). In another embodiment, the at least one ionic surfactant consists of sodium dodecyl sulfate (SDS). In still another embodiment, the at least one ionic surfactant comprises cetyl trimethylammonium bromide (CTAB). In yet another embodiment, the at least one surfactant consists of cetyl trimethylammonium bromide (CTAB).

The weight ratio of the crystalline steviol glycoside composition comprising rebaudioside M to surfactant can be from about 20:1 to about 1:20, such as, for example, from about 10:1 to about 1:10, from about 10:1 to about 1:1, from about 10:1 to about 3;1, from about 5:1 to about 1:1, about 4:1 to about 1:1, about 3:1 to about 1:1, or about 2:1 to about 1:1.

In a particular embodiment, the weight ratio of the crystalline steviol glycoside composition comprising rebaudioside M to surfactant is from about 5:1 to about 1:1, such as, for example, from about 3:1 to about 1:1.

In another embodiment, the mole ratio of the crystalline steviol glycoside composition comprising rebaudioside M to surfactant is from about 2:1 to about 1:1.

In some embodiments, the mixture is heated to a temperature from about 40° C. to about 110° C., such as, for example, from about 40° C. to about 100° C., from about 40° C. to about 90° C., from about 40° C. to about 80° C., from about 40° C. to about 70° C., from about 40° C. to about 60° C., from about 40° C. to about 50° C., from about 50° C. to about 100° C., from about 50° C. to about 90° C., from about 50° C. to about 80° C., from about 50° C. to about 70° C., from about 50° C. to about 60° C., from about 60° C. to about 100° C., from about 60° C. to about 100° C., from about 60° C. to about 90° C., from about 60° C. to about 80° C., from about 60° C. to about 70° C., from about 70° C. to about 110° C., from about 70° C. to about 100° C., from about 70° C. to about 90° C., from about 70° C. to about 80° C., from about 80° C. to about 110° C., from about 80° C. to about 100° C., from about 80° C. to about 90° C., from about 90° C. to about 110° C., from about 90° C. to about 100° C. and from about 100° C. to about 110° C. In a particular embodiment, the mixture is heated to a temperature that does not exceed about 70° C.

The crystalline steviol glycoside composition typically comprises a majority rebaudioside M. The remainder of the composition largely comprises other steviol glycosides, including, but are not limited to, rebaudioside D, rebaudioside A, rebaudioside N, rebaudioside O, rebaudioside E, steviolmonoside, steviolbioside, rubusoside, dulcoside B, dulcoside A, rebaudioside B, rebaudioside G, stevioside, rebaudioside C, rebaudioside F, rebaudioside I, rebaudioside H, rebaudioside L, rebaudioside K, rebaudioside J, rebaudioside M2, rebaudioside D2, rebaudioside S, rebaudioside T, rebaudioside U, rebaudioside V, rebaudioside W, rebaudioside Z1, rebaudioside Z2, rebaudioside IX, enzymatically glucosylated steviol glycosides and combinations thereof.

The steviol glycoside can be natural, synthetic or a combination of natural and synthetic.

The crystalline steviol glycoside composition can be provided in pure form or as part of a mixture, i.e. a steviol glycoside blend.

The crystalline steviol glycoside composition comprises at least about 50% rebaudioside M by weight, such as, for example, from about 50% to about 90%, from about 50% to about 80%, from about 50% to about 70%, from about 50% to about 60%, from about 60% to about 90%, from about 60% to about 80%, from about 60% to about 70%, from about 70% to about 90%, from about 70% to about 80% and from about 80% to about 90%.

In a particular embodiment, the crystalline steviol glycoside composition comprises at least about 80% rebaudioside M by weight. In another particular embodiment, the crystalline steviol glycoside composition comprises at least about 90% rebaudioside M by weight. In still another particular embodiment, the crystalline steviol glycoside composition comprises at least about 95% rebaudioside M by weight.

In other embodiments, the crystalline steviol glycoside composition has a total steviol glycoside content of about 95% by weight or greater on a dry basis. The remaining 5% comprises other non-steviol glycoside compounds, e.g. by-products from extraction or purification processes. In some embodiments, the crystalline steviol glycoside composition has a total steviol glycoside content of about 96% or greater, about 97% or greater, about 98% or greater or about 99% or greater.

The present method provides a concentrate that is clear by visual inspection. In some embodiments, no further processing is required, and the cooled concentrate can be further processed into a beverage syrup.

In other embodiments, particularly those with higher wt % s, the cooled concentrate is heated again for at least two hours to ensure dissolution and long-term stability, such as, for example, from about two hours to about 24 hours, from about 2 hours to about 12 hours, from about 2 hours to about 8 hours, from about 5 hours to about 24 hours, from about 5 hours to about 12 hours, from about 10 hours to about 24 hours, from about 15 hours to about 24 hours and from about 20 to about 24 hours.

The second heating step is preferably done without stirring, e.g. in an oven or similar device.

The cooled concentrate is heated to a temperature from about 50° C. to about 110° C., such as, for example, from about 50° C. to about 100° C., from about 50° C. to about 90° C., from about 50° C. to about 80° C., from about 50° C. to about 70° C., from about 50° C. to about 60° C., from about 60° C. to about 100° C., from about 60° C. to about 100° C., from about 60° C. to about 90° C., from about 60° C. to about 80° C., from about 60° C. to about 70° C., from about 70° C. to about 110° C., from about 70° C. to about 100° C., from about 70° C. to about 90° C., from about 70° C. to about 80° C., from about 80° C. to about 110° C., from about 80° C. to about 100° C., from about 80° C. to about 90° C., from about 90° C. to about 110° C., from about 90° C. to about 100° C. and from about 100° C. to about 110° C.

After the concentrate is heated for the desired amount of time, it is cooled, e.g. to room temperature.

The final concentrate is clear by visual inspection, i.e. no particulate material is observed, for at least about 72 hours after preparing. In some embodiments, the final concentrate is clear by visual inspection for at least 4 days, at least 14 days or at least 24 days.

The final concentrate prepared by the process described herein is also stable for at least 72 hours after preparing, i.e. the steviol glycoside content is unchanged (statistically) when measured by, e.g. HPLC. In some embodiments, the final concentrate is stable for at least 4 days, at least 14 days or at least 24 days.

II. Beverage Syrup and Method of Making Same

The present invention also provides beverage syrups prepared using the concentrate described herein and methods for making beverage syrups.

In one embodiment, a method of making a beverage syrup comprises combining beverage syrup ingredients with a concentrate prepared by the method above. In one embodiment, the beverage syrup ingredients are added to the concentrate to provide a beverage syrup.

In other embodiments, the concentrate can be diluted prior to combination with beverage syrup ingredients. The dilution can be done at once or in a serial fashion. The temperature for dilution is preferably the same temperature at which the beverage syrup ingredients are formulated, typically room temperature—but not above about 70° C. for steviol glycosides or other thermally sensitive ingredients.

The skilled practitioner recognizes that beverage syrup ingredients can be added singularly or in combination. Also, solutions of dry beverage syrup ingredients can be made and used to add to the bulk quantity of water. Beverage syrup ingredients typically are added to the bulk quantity of water in an order that minimizes potential adverse interactions between ingredients or potential adverse effect on an ingredient. For example, nutrients that are temperature-sensitive might be added during a relatively low-temperature portion toward the end of the manufacturing process. Similarly, flavors and flavor compounds often are added just before completion of the syrup to minimize potential loss of volatile components and to minimize flavor loss in any form. Often, acidification is one of the last steps, typically carried out before temperature-sensitive, volatile, and flavor materials are added. Thus, flavors or flavor components or other volatile materials and nutrients typically are added at an appropriate time and at an appropriate temperature.

Beverage syrup ingredients include, but are not limited to, additional sweeteners, functional ingredients and additives.

The additional sweetener can be a natural sweetener, a natural high potency sweetener or synthetic sweetener.

As used herein, the phrase "natural high potency sweetener" refers to any sweetener found naturally in nature and characteristically has a sweetness potency greater than sucrose, fructose, or glucose, yet has less calories. The natural high potency sweetener can be provided as a pure compound or, alternatively, as part of an extract. As used herein, the phrase "synthetic sweetener" refers to any composition which is not found naturally in nature and characteristically has a sweetness potency greater than sucrose, fructose, or glucose, yet has less calories.

In one embodiment, the sweetener is a carbohydrate sweetener. Suitable carbohydrate sweeteners include, but not limited to, the group consisting of sucrose, glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, fucose, rhamnose, arabinose, turanose, sialose and combinations thereof.

Other suitable sweeteners include siamenoside, monatin and its salts (monatin SS, RR, RS, SR), curculin, mogrosides, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides (GSGs) and combinations thereof.

In one embodiment, the sweetener is a caloric sweetener or mixture of caloric sweeteners. In another embodiment, the caloric sweetener is selected from sucrose, fructose, glucose, high fructose corn/starch syrup, a beet sugar, a cane sugar, and combinations thereof.

In another embodiment, the sweetener is a rare sugar selected from allulose, gulose, kojibiose, sorbose, lyxose, ribulose, xylose, xylulose, D-allose, L-ribose, D-tagatose, L-glucose, L-fucose, L-arabinose, turanose and combinations thereof.

The amount of additional sweetener in the beverage syrup can vary. In one embodiment, the beverage syrup comprises from about 1 ppm to about 10 wt % additional sweetener(s).

Exemplary functional ingredients include, but are not limited to, saponins, antioxidants, dietary fiber sources, fatty acids, vitamins, glucosamine, minerals, preservatives, hydration agents, probiotics, prebiotics, weight management agents, osteoporosis management agents, phytoestrogens, long chain primary aliphatic saturated alcohols, phytosterols and combinations thereof.

In certain embodiments, the functional ingredient is at least one saponin. As used herein, the at least one saponin may comprise a single saponin or a plurality of saponins as a functional ingredient for the composition provided herein. Saponins are glycosidic natural plant products comprising an aglycone ring structure and one or more sugar moieties. Non-limiting examples of specific saponins for use in particular embodiments of the invention include group A acetyl saponin, group B acetyl saponin, and group E acetyl saponin. Several common sources of saponins include soybeans, which have approximately 5% saponin content by dry weight, soapwort plants (*Saponaria*), the root of which was used historically as soap, as well as alfalfa, aloe, asparagus, grapes, chickpeas, *yucca*, and various other beans and weeds. Saponins may be obtained from these sources by using extraction techniques well known to those of ordinary skill in the art. A description of conventional extraction techniques can be found in U.S. Pat. Appl. No. 2005/0123662.

In certain embodiments, the functional ingredient is at least one antioxidant. As used herein, "antioxidant" refers to any substance which inhibits, suppresses, or reduces oxidative damage to cells and biomolecules.

Examples of suitable antioxidants for embodiments of this invention include, but are not limited to, vitamins, vitamin cofactors, minerals, hormones, carotenoids, carotenoid terpenoids, non-carotenoid terpenoids, flavonoids, flavonoid polyphenolics (e.g., bioflavonoids), flavonols, flavones, phenols, polyphenols, esters of phenols, esters of polyphenols, nonflavonoid phenolics, isothiocyanates, and combinations thereof. In some embodiments, the antioxidant is vitamin A, vitamin C, vitamin E, ubiquinone, mineral selenium, manganese, melatonin, α-carotene, β-carotene, lycopene, lutein, zeanthin, crypoxanthin, reservatol, eugenol, quercetin, catechin, gossypol, hesperetin, curcumin, ferulic acid, thymol, hydroxytyrosol, tumeric, thyme, olive oil, lipoic acid, glutathinone, gutamine, oxalic acid, tocopherol-derived compounds, butylated hydroxyanisole (BHA), butylated hydroxytoluene (BHT), ethylenediaminetetraacetic acid (EDTA), tert-butylhydroquinone, acetic acid, pectin, tocotrienol, tocopherol, coenzyme Q10, zeaxanthin, astaxanthin, canthaxantin, saponins, limonoids, kaempfedrol, myricetin, isorhamnetin, proanthocyanidins, quercetin, rutin, luteolin, apigenin, tangeritin, hesperetin, naringenin, erodictyol, flavan-3-ols (e.g., anthocyanidins), gallocatechins, epicatechin and its gallate forms, epigallocatechin and its gallate forms (ECGC) theaflavin and its gallate forms, thearubigins, isoflavone, phytoestrogens, genistein, daidzein, glycitein, anythocyanins, cyaniding, delphinidin, malvidin, pelargonidin, peonidin, petunidin, ellagic acid, gallic acid, salicylic acid, rosmarinic acid, cinnamic acid and its derivatives (e.g., ferulic acid), chlorogenic acid, chicoric acid, gallotannins, ellagitannins, anthoxanthins, betacyanins and other plant pigments, silymarin, citric acid, lignan, antinutrients, bilirubin, uric acid, R-α-lipoic acid, N-acetylcysteine, emblicanin, apple extract, apple skin extract (applephenon), rooibos extract red, rooibos extract, green, hawthorn berry extract, red raspberry extract, green coffee antioxidant (GCA), aronia extract 20%, grape seed extract (VinOseed), cocoa extract, hops extract, mangosteen extract, mangosteen hull extract, cranberry extract, pomegranate extract, pomegranate hull extract, pomegranate seed extract, hawthorn berry extract, pomella pomegranate extract, cinnamon bark extract, grape skin extract, bilberry extract, pine bark extract, pycnogenol, elderberry extract, mulberry root extract, wolfberry (gogi) extract, blackberry extract, blueberry extract, blueberry leaf extract, raspberry extract, turmeric extract, citrus bioflavonoids, black currant, ginger, acai powder, green coffee bean extract, green tea extract, and phytic acid, or combinations thereof. In alternate embodiments, the antioxidant is a synthetic antioxidant such as butylated hydroxytolune or butylated hydroxyanisole, for example. Other sources of suitable antioxidants for embodiments of this invention include, but are not limited to, fruits, vegetables, tea, cocoa, chocolate, spices, herbs, rice, organ meats from livestock, yeast, whole grains, or cereal grains.

Particular antioxidants belong to the class of phytonutrients called polyphenols (also known as "polyphenolics"), which are a group of chemical substances found in plants, characterized by the presence of more than one phenol group per molecule. Suitable polyphenols for embodiments of this invention include catechins, proanthocyanidins, procyanidins, anthocyanins, quercerin, rutin, reservatrol, isoflavones, curcumin, punicalagin, ellagitannin, hesperidin, naringin, citrus flavonoids, chlorogenic acid, other similar materials, and combinations thereof.

In one embodiment, the antioxidant is a catechin such as, for example, epigallocatechin gallate (EGCG). In another embodiment, the antioxidant is chosen from proanthocyanidins, procyanidins or combinations thereof. In particular embodiments, the antioxidant is an anthocyanin. In still other embodiments, the antioxidant is chosen from quercetin, rutin or combinations thereof. In one embodiment, the antioxidant is reservatrol. In another embodiment, the antioxidant is an isoflavone. In still another embodiment, the antioxidant is curcumin. In a yet further embodiment, the antioxidant is chosen from punicalagin, ellagitannin or combinations thereof. In a still further embodiment, the antioxidant is chlorogenic acid.

In certain embodiments, the functional ingredient is at least one dietary fiber. Numerous polymeric carbohydrates having significantly different structures in both composition and linkages fall within the definition of dietary fiber. Such compounds are well known to those skilled in the art, non-limiting examples of which include non-starch polysaccharides, lignin, cellulose, methylcellulose, the hemicelluloses, β-glucans, pectins, gums, mucilage, waxes, inulins, oligosaccharides, fructooligosaccharides, cyclodextrins, chitins, and combinations thereof. Although dietary fiber generally is derived from plant sources, indigestible animal products such as chitins are also classified as dietary fiber. Chitin is a polysaccharide composed of units of acetylglucosamine joined by β(1-4) linkages, similar to the linkages of cellulose.

In certain embodiments, the functional ingredient is at least one fatty acid. As used herein, "fatty acid" refers to any straight chain monocarboxylic acid and includes saturated fatty acids, unsaturated fatty acids, long chain fatty acids, medium chain fatty acids, short chain fatty acids, fatty acid precursors (including omega-9 fatty acid precursors), and esterified fatty acids. As used herein, "long chain polyunsaturated fatty acid" refers to any polyunsaturated carboxylic acid or organic acid with a long aliphatic tail. As used herein, "omega-3 fatty acid" refers to any polyunsaturated fatty acid having a first double bond as the third carbon-carbon bond from the terminal methyl end of its carbon chain. In particular embodiments, the omega-3 fatty acid may comprise a long chain omega-3 fatty acid. As used herein, "omega-6 fatty acid" any polyunsaturated fatty acid having a first double bond as the sixth carbon-carbon bond from the terminal methyl end of its carbon chain.

Suitable omega-3 fatty acids for use in embodiments of the present invention can be derived from algae, fish, animals, plants, or combinations thereof, for example. Examples of suitable omega-3 fatty acids include, but are not limited to, linolenic acid, alpha-linolenic acid, eicosapentaenoic acid, docosahexaenoic acid, stearidonic acid, eicosatetraenoic acid and combinations thereof. In some embodiments, suitable omega-3 fatty acids can be provided in fish oils, (e.g., menhaden oil, tuna oil, salmon oil, bonito oil, and cod oil), microalgae omega-3 oils or combinations thereof. In particular embodiments, suitable omega-3 fatty acids may be derived from commercially available omega-3 fatty acid oils such as Microalgae DHA oil (from Martek, Columbia, MD), OmegaPure (from Omega Protein, Houston, TX), Marinol C-38 (from Lipid Nutrition, Channahon, IL), Bonito oil and MEG-3 (from Ocean Nutrition, Dartmouth, NS), Evogel (from Symrise, Holzminden, Germany), Marine Oil, from tuna or salmon (from Arista Wilton, CT), OmegaSource 2000, Marine Oil, from menhaden and Marine Oil, from cod (from OmegaSource, RTP, NC).

Suitable omega-6 fatty acids include, but are not limited to, linoleic acid, gamma-linolenic acid, dihommo-gamma-linolenic acid, arachidonic acid, eicosadienoic acid, docosadienoic acid, adrenic acid, docosapentaenoic acid and combinations thereof.

Suitable esterified fatty acids for embodiments of the present invention include, but are not limited to, monoacylglycerols containing omega-3 and/or omega-6 fatty acids, diacylglycerols containing omega-3 and/or omega-6 fatty acids, or triacylglycerols containing omega-3 and/or omega-6 fatty acids and combinations thereof.

In certain embodiments, the functional ingredient is at least one vitamin. Suitable vitamins include, vitamin A, vitamin D, vitamin E, vitamin K, vitamin B1, vitamin B2, vitamin B3, vitamin B5, vitamin B6, vitamin B7, vitamin B9, vitamin B12, and vitamin C.

Various other compounds have been classified as vitamins by some authorities. These compounds may be termed pseudo-vitamins and include, but are not limited to, compounds such as ubiquinone (coenzyme Q10), pangamic acid, dimethylglycine, taestrile, amygdaline, flavanoids, para-aminobenzoic acid, adenine, adenylic acid, and s-methylmethionine. As used herein, the term vitamin includes pseudo-vitamins. In some embodiments, the vitamin is a fat-soluble vitamin chosen from vitamin A, D, E, K and combinations thereof. In other embodiments, the vitamin is a water-soluble vitamin chosen from vitamin B1, vitamin B2, vitamin B3, vitamin B6, vitamin B12, folic acid, biotin, pantothenic acid, vitamin C and combinations thereof.

In certain embodiments, the functional ingredient is glucosamine, optionally further comprising chondroitin sulfate.

In certain embodiments, the functional ingredient is at least one mineral. Minerals, in accordance with the teachings of this invention, comprise inorganic chemical elements required by living organisms. Minerals are comprised of a broad range of compositions (e.g., elements, simple salts, and complex silicates) and also vary broadly in crystalline structure. They may naturally occur in foods and beverages, may be added as a supplement, or may be consumed or administered separately from foods or beverages.

Minerals may be categorized as either bulk minerals, which are required in relatively large amounts, or trace minerals, which are required in relatively small amounts. Bulk minerals generally are required in amounts greater than or equal to about 100 mg per day and trace minerals are those that are required in amounts less than about 100 mg per day.

In one embodiment, the mineral is chosen from bulk minerals, trace minerals or combinations thereof. Non-limiting examples of bulk minerals include calcium, chlorine, magnesium, phosphorous, potassium, sodium, and sulfur. Non-limiting examples of trace minerals include chromium, cobalt, copper, fluorine, iron, manganese, molybdenum, selenium, zinc, and iodine. Although iodine generally is classified as a trace mineral, it is required in larger quantities than other trace minerals and often is categorized as a bulk mineral.

In a particular embodiment, the mineral is a trace mineral, believed to be necessary for human nutrition, non-limiting examples of which include bismuth, boron, lithium, nickel, rubidium, silicon, strontium, tellurium, tin, titanium, tungsten, and vanadium.

The minerals embodied herein may be in any form known to those of ordinary skill in the art. For example, in one embodiment, the minerals may be in their ionic form, having either a positive or negative charge. In another embodiment, the minerals may be in their molecular form. For example, sulfur and phosphorous often are found naturally as sulfates, sulfides, and phosphates.

In certain embodiments, the functional ingredient is at least one preservative. In particular embodiments, the preservative is chosen from antimicrobials, antioxidants, antienzymatics or combinations thereof. Non-limiting examples of antimicrobials include sulfites, propionates, benzoates, sorbates, nitrates, nitrites, bacteriocins, salts, sugars, acetic acid, dimethyl dicarbonate (DMDC), ethanol, and ozone. In one embodiment, the preservative is a sulfite. Sulfites include, but are not limited to, sulfur dioxide, sodium bisulfite, and potassium hydrogen sulfite. In another embodiment, the preservative is a propionate. Propionates include, but are not limited to, propionic acid, calcium propionate, and sodium propionate. In yet another embodiment, the preservative is a benzoate. Benzoates include, but are not limited to, sodium benzoate and benzoic acid. In still another embodiment, the preservative is a sorbate. Sorbates include, but are not limited to, potassium sorbate, sodium sorbate, calcium sorbate, and sorbic acid. In a still further embodiment, the preservative is a nitrate and/or a nitrite. Nitrates and nitrites include, but are not limited to, sodium nitrate and sodium nitrite. In another embodiment, the at least one preservative is a bacteriocin, such as, for example, nisin. In still another embodiment, the preservative is ethanol. In yet another embodiment, the preservative is ozone. Non-limiting examples of antienzymatics suitable for use as preservatives in particular embodiments of the invention include ascorbic acid, citric acid, and metal chelating agents such as ethylenediaminetetraacetic acid (EDTA).

In certain embodiments, the functional ingredient is at least one hydration agent. In a particular embodiment, the hydration agent is an electrolyte. Non-limiting examples of electrolytes include sodium, potassium, calcium, magnesium, chloride, phosphate, bicarbonate, and combinations thereof. Suitable electrolytes for use in particular embodiments of this invention are also described in U.S. Pat. No. 5,681,569. In one embodiment, the electrolyte is obtained from the corresponding water-soluble salt. Non-limiting examples of salts include chlorides, carbonates, sulfates, acetates, bicarbonates, citrates, phosphates, hydrogen phosphates, tartrates, sorbates, citrates, benzoates, or combinations thereof. In other embodiments, the electrolyte is provided by juice, fruit extracts, vegetable extracts, tea, or tea extracts.

In another particular embodiment, the hydration agent is a carbohydrate to supplement energy stores burned by muscles. Suitable carbohydrates for use in particular embodiments of this invention are described in U.S. Pat. Nos. 4,312,856, 4,853,237, 5,681,569, and 6,989,171. Non-limiting examples of suitable carbohydrates include monosaccharides, disaccharides, oligosaccharides, complex polysaccharides or combinations thereof. Non-limiting examples of suitable types of monosaccharides for use in particular embodiments include trioses, tetroses, pentoses, hexoses, heptoses, octoses, and nonoses. Non-limiting examples of specific types of suitable monosaccharides include glyceraldehyde, dihydroxyacetone, erythrose, threose, erythrulose, arabinose, lyxose, ribose, xylose, ribulose, xylulose, allose, altrose, galactose, glucose, gulose, idose, mannose, talose, fructose, psicose, sorbose, tagatose, mannoheptulose, sedoheltulose, octolose, and sialose. Non-limiting examples of suitable disaccharides include sucrose, lactose, and maltose. Non-limiting examples of suitable oligosaccharides include saccharose, maltotriose, and maltodextrin. In other particular embodiments, the carbohydrates are provided by a corn syrup, a beet sugar, a cane sugar, a juice, or a tea.

In another particular embodiment, the hydration agent is a flavanol that provides cellular rehydration. Flavanols are a class of natural substances present in plants, and generally comprise a 2-phenylbenzopyrone molecular skeleton attached to one or more chemical moieties. Non-limiting examples of suitable flavanols for use in particular embodiments of this invention include catechin, epicatechin, gallocatechin, epigallocatechin, epicatechin gallate, epigallocatechin 3-gallate, theaflavin, theaflavin 3-gallate, theaflavin 3'-gallate, theaflavin 3,3' gallate, thearubigin or combinations thereof. Several common sources of flavanols include tea plants, fruits, vegetables, and flowers. In preferred embodiments, the flavanol is extracted from green tea.

In a particular embodiment, the hydration agent is a glycerol solution to enhance exercise endurance. The ingestion of a glycerol containing solution has been shown to provide beneficial physiological effects, such as expanded blood volume, lower heart rate, and lower rectal temperature.

In certain embodiments, the functional ingredient is chosen from at least one probiotic, prebiotic and combination thereof. The probiotic is a beneficial microorganism that affects the human body's naturally-occurring gastrointestinal microflora. Examples of probiotics include, but are not limited to, bacteria of the genus Lactobacilli, Bifidobacteria, Streptococci, or combinations thereof, that confer beneficial effects to humans. In particular embodiments of the invention, the at least one probiotic is chosen from the genus Lactobacilli. According to other particular embodiments of this invention, the probiotic is chosen from the genus Bifidobacteria. In a particular embodiment, the probiotic is chosen from the genus *Streptococcus*.

Probiotics that may be used in accordance with this invention are well-known to those of skill in the art. Non-limiting examples of foodstuffs comprising probiotics include yogurt, sauerkraut, kefir, kimchi, fermented vegetables, and other foodstuffs containing a microbial element that beneficially affects the host animal by improving the intestinal microbalance.

Prebiotics, in accordance with the embodiments of this invention, include, without limitation, mucopolysaccharides, oligosaccharides, polysaccharides, amino acids, vitamins, nutrient precursors, proteins and combinations thereof. According to a particular embodiment of this invention, the prebiotic is chosen from dietary fibers, including, without limitation, polysaccharides and oligosaccharides. Non-limiting examples of oligosaccharides that are categorized as prebiotics in accordance with particular embodiments of this invention include fructooligosaccharides, inulins, isomalto-oligosaccharides, lactilol, lactosucrose, lactulose, pyrodextrins, soy oligosaccharides, transgalacto-oligosaccharides, and xylo-oligosaccharides. In other embodiments, the prebiotic is an amino acid. Although a number of known prebiotics break down to provide carbohydrates for probiotics, some probiotics also require amino acids for nourishment.

Prebiotics are found naturally in a variety of foods including, without limitation, bananas, berries, asparagus, garlic, wheat, oats, barley (and other whole grains), flaxseed, tomatoes, Jerusalem artichoke, onions and chicory, greens (e.g., dandelion greens, spinach, collard greens, chard, kale, mustard greens, turnip greens), and legumes (e.g., lentils, kidney beans, chickpeas, navy beans, white beans, black beans).

In certain embodiments, the functional ingredient is at least one weight management agent. As used herein, "a weight management agent" includes an appetite suppressant and/or a thermogenesis agent. As used herein, the phrases "appetite suppressant", "appetite satiation compositions", "satiety agents", and "satiety ingredients" are synonymous. The phrase "appetite suppressant" describes macronutrients, herbal extracts, exogenous hormones, anorectics, anorexigenics, pharmaceutical drugs, and combinations thereof, that when delivered in an effective amount, suppress, inhibit, reduce, or otherwise curtail a person's appetite. The phrase "thermogenesis agent" describes macronutrients, herbal extracts, exogenous hormones, anorectics, anorexigenics, pharmaceutical drugs, and combinations thereof, that when delivered in an effective amount, activate or otherwise enhance a person's thermogenesis or metabolism.

Suitable weight management agents include macronutrients selected from the group consisting of proteins, carbohydrates, dietary fats, and combinations thereof. Consumption of proteins, carbohydrates, and dietary fats stimulates the release of peptides with appetite-suppressing effects. For example, consumption of proteins and dietary fats stimulates the release of the gut hormone cholecytokinin (CCK), while consumption of carbohydrates and dietary fats stimulates release of Glucagon-like peptide 1 (GLP-1).

Suitable macronutrient weight management agents also include carbohydrates. Carbohydrates generally comprise sugars, starches, cellulose and gums that the body converts into glucose for energy. Carbohydrates often are classified into two categories, digestible carbohydrates (e.g., monosaccharides, disaccharides, and starch) and non-digestible carbohydrates (e.g., dietary fiber). Studies have shown that non-digestible carbohydrates and complex polymeric carbohydrates having reduced absorption and digestibility in the small intestine stimulate physiologic responses that inhibit food intake. Accordingly, the carbohydrates embodied herein desirably comprise non-digestible carbohydrates or carbohydrates with reduced digestibility. Non-limiting examples of such carbohydrates include polydextrose; inulin; monosaccharide-derived polyols such as erythritol, mannitol, xylitol, and sorbitol; disaccharide-derived alcohols such as isomalt, lactitol, and maltitol; and hydrogenated starch hydrolysates. Carbohydrates are described in more detail herein below.

In another particular embodiment, the weight management agent is a dietary fat. Dietary fats are lipids comprising combinations of saturated and unsaturated fatty acids. Poly-unsaturated fatty acids have been shown to have a greater satiating power than mono-unsaturated fatty acids. Accordingly, the dietary fats embodied herein desirably comprise poly-unsaturated fatty acids, non-limiting examples of which include triacylglycerols.

In another particular embodiment, the weight management agent is an herbal extract. Extracts from numerous types of plants have been identified as possessing appetite suppressant properties. Non-limiting examples of plants whose extracts have appetite suppressant properties include plants of the genus *Hoodia, Trichocaulon, Caralluma, Stapelia, Orbea, Asclepias*, and *Camelia*. Other embodiments include extracts derived from *Gymnema sylvestre*, Kola Nut, *Citrus aurantium, Yerba mate, Griffonia simplicifolia*, Guarana, myrrh, guggul Lipid, and black current seed oil.

The herbal extracts may be prepared from any type of plant material or plant biomass. Non-limiting examples of plant material and biomass include the stems, roots, leaves, dried powder obtained from the plant material, and sap or dried sap. The herbal extracts generally are prepared by extracting sap from the plant and then spray-drying the sap. Alternatively, solvent extraction procedures may be employed. Following the initial extraction, it may be desirable to further fractionate the initial extract (e.g., by column chromatography) in order to obtain an herbal extract with enhanced activity. Such techniques are well known to those of ordinary skill in the art.

In one embodiment, the herbal extract is derived from a plant of the genus *Hoodia*. A sterol glycoside of *Hoodia*, known as P57, is believed to be responsible for the appetite-suppressant effect of the *Hoodia* species. In another embodiment, the herbal extract is derived from a plant of the genus *Caralluma*, non-limiting examples of which include caratuberside A, caratuberside B, bouceroside I, bouceroside II, bouceroside III, bouceroside IV, bouceroside V, bouceroside VI, bouceroside VII, bouceroside VIII, bouceroside IX, and bouceroside X. In another embodiment, the at least one herbal extract is derived from a plant of the genus *Trichocaulon*. *Trichocaulon* plants are succulents that generally are native to southern Africa, similar to *Hoodia*, and include the species *T. piliferum* and *T. officinale*. In another embodiment, the herbal extract is derived from a plant of the genus *Stapelia* or *Orbea*. Not wishing to be bound by any theory, it is believed that the compounds exhibiting appetite suppressant activity are saponins, such as pregnane glycosides, which include stavarosides A, B, C, D, E, F, G, H, I, J, and K. In another embodiment, the herbal extract is derived from a plant of the genus *Asclepias*. Not wishing to be bound by any theory, it is believed that the extracts comprise steroidal compounds, such as pregnane glycosides and pregnane aglycone, having appetite suppressant effects.

In another particular embodiment, the weight management agent is an exogenous hormone having a weight management effect. Non-limiting examples of such hormones include CCK, peptide YY, ghrelin, bombesin and gastrin-releasing peptide (GRP), enterostatin, apolipoprotein A-IV, GLP-1, amylin, somastatin, and leptin.

In another embodiment, the weight management agent is a pharmaceutical drug. Non-limiting examples include phentenime, diethylpropion, phendimetrazine, sibutramine, rimonabant, oxyntomodulin, floxetine hydrochloride, ephedrine, phenethylamine, or other stimulants.

In certain embodiments, the functional ingredient is at least one osteoporosis management agent. In certain embodiments, the osteoporosis management agent is at least one calcium source. According to a particular embodiment, the calcium source is any compound containing calcium, including salt complexes, solubilized species, and other forms of calcium. Non-limiting examples of calcium sources include amino acid chelated calcium, calcium carbonate, calcium oxide, calcium hydroxide, calcium sulfate, calcium chloride, calcium phosphate, calcium hydrogen phosphate, calcium dihydrogen phosphate, calcium citrate, calcium malate, calcium citrate malate, calcium gluconate, calcium tartrate, calcium lactate, solubilized species thereof, and combinations thereof.

According to a particular embodiment, the osteoporosis management agent is a magnesium source. The magnesium source is any compound containing magnesium, including salt complexes, solubilized species, and other forms of magnesium. Non-limiting examples of magnesium sources include magnesium chloride, magnesium citrate, magnesium gluceptate, magnesium gluconate, magnesium lactate, magnesium hydroxide, magnesium picolate, magnesium sulfate, solubilized species thereof, and mixtures thereof. In another particular embodiment, the magnesium source comprises an amino acid chelated or creatine chelated magnesium.

In other embodiments, the osteoporosis agent is chosen from vitamins D, C, K, their precursors and/or beta-carotene and combinations thereof.

Numerous plants and plant extracts also have been identified as being effective in the prevention and treatment of osteoporosis. Non-limiting examples of suitable plants and plant extracts as osteoporosis management agents include species of the genus *Taraxacum* and *Amelanchier*, as disclosed in U.S. Patent Publication No. 2005/0106215, and species of the genus *Lindera, Artemisia, Acorus, Carthamus, Carum, Cnidium, Curcuma, Cyperus, Juniperus, Prunus, Iris, Cichorium, Dodonaea, Epimedium, Erigonoum, Soya, Mentha, Ocimum, Thymus, Tanacetum, Plantago,* Spear-

*mint*, *Bixa*, *Vitis*, *Rosemarinus*, *Rhus*, and *Anethum*, as disclosed in U.S. Patent Publication No. 2005/0079232.

In certain embodiments, the functional ingredient is at least one phytoestrogen. Phytoestrogens are compounds found in plants which can typically be delivered into human bodies by ingestion of the plants or the plant parts having the phytoestrogens. As used herein, "phytoestrogen" refers to any substance which, when introduced into a body causes an estrogen-like effect of any degree. For example, a phytoestrogen may bind to estrogen receptors within the body and have a small estrogen-like effect.

Examples of suitable phytoestrogens for embodiments of this invention include, but are not limited to, isoflavones, stilbenes, lignans, resorcyclic acid lactones, coumestans, coumestrol, equol, and combinations thereof. Sources of suitable phytoestrogens include, but are not limited to, whole grains, cereals, fibers, fruits, vegetables, black cohosh, agave root, black currant, black haw, chasteberries, cramp bark, dong quai root, devil's club root, false unicorn root, *ginseng* root, groundsel herb, licorice, liferoot herb, motherwort herb, peony root, raspberry leaves, rose family plants, sage leaves, sarsaparilla root, saw palmetto berried, wild yam root, yarrow blossoms, legumes, soybeans, soy products (e.g., miso, soy flour, soymilk, soy nuts, soy protein isolate, tempen, or tofu) chick peas, nuts, lentils, seeds, clover, red clover, dandelion leaves, dandelion roots, fenugreek seeds, green tea, hops, red wine, flaxseed, garlic, onions, linseed, borage, butterfly weed, caraway, chaste tree, vitex, dates, dill, fennel seed, gotu kola, milk thistle, pennyroyal, pomegranates, southernwood, soya flour, tansy, and root of the kudzu vine (*Pueraria* root) and the like, and combinations thereof.

Isoflavones belong to the group of phytonutrients called polyphenols. In general, polyphenols (also known as "polyphenolics"), are a group of chemical substances found in plants, characterized by the presence of more than one phenol group per molecule.

Suitable phytoestrogen isoflavones in accordance with embodiments of this invention include genistein, daidzein, glycitein, biochanin A, formononetin, their respective naturally occurring glycosides and glycoside conjugates, matairesinol, secoisolariciresinol, enterolactone, enterodiol, textured vegetable protein, and combinations thereof.

Suitable sources of isoflavones for embodiments of this invention include, but are not limited to, soy beans, soy products, legumes, alfalfa sprouts, chickpeas, peanuts, and red clover.

In certain embodiments, the functional ingredient is at least one long chain primary aliphatic saturated alcohol. Long-chain primary aliphatic saturated alcohols are a diverse group of organic compounds. The term alcohol refers to the fact these compounds feature a hydroxyl group (—OH) bound to a carbon atom. Non-limiting examples of particular long-chain primary aliphatic saturated alcohols for use in particular embodiments of the invention include the 8 carbon atom 1-octanol, the 9 carbon 1-nonanol, the 10 carbon atom 1-decanol, the 12 carbon atom 1-dodecanol, the 14 carbon atom 1-tetradecanol, the 16 carbon atom 1-hexadecanol, the 18 carbon atom 1-octadecanol, the 20 carbon atom 1-eicosanol, the 22 carbon 1-docosanol, the 24 carbon 1-tetracosanol, the 26 carbon 1-hexacosanol, the 27 carbon 1-heptacosanol, the 28 carbon 1-octanosol, the 29 carbon 1-nonacosanol, the 30 carbon 1-triacontanol, the 32 carbon 1-dotriacontanol, and the 34 carbon 1-tetracontanol.

In one embodiment, the long-chain primary aliphatic saturated alcohol is a policosanol. Policosanol is the term for a mixture of long-chain primary aliphatic saturated alcohols composed primarily of 28 carbon 1-octanosol and 30 carbon 1-triacontanol, as well as other alcohols in lower concentrations such as 22 carbon 1-docosanol, 24 carbon 1-tetracosanol, 26 carbon 1-hexacosanol, 27 carbon 1-heptacosanol, 29 carbon 1-nonacosanol, 32 carbon 1-dotriacontanol, and 34 carbon 1-tetracontanol.

In certain embodiments, the functional ingredient is at least one phytosterol, phytostanol or combination thereof. As used herein, the phrases "stanol", "plant stanol" and "phytostanol" are synonymous. Plant sterols and stanols are present naturally in small quantities in many fruits, vegetables, nuts, seeds, cereals, legumes, vegetable oils, bark of the trees and other plant sources. Sterols are a subgroup of steroids with a hydroxyl group at C-3. Generally, phytosterols have a double bond within the steroid nucleus, like cholesterol; however, phytosterols also may comprise a substituted side chain (R) at C-24, such as an ethyl or methyl group, or an additional double bond. The structures of phytosterols are well known to those of skill in the art.

At least 44 naturally-occurring phytosterols have been discovered, and generally are derived from plants, such as corn, soy, wheat, and wood oils; however, they also may be produced synthetically to form compositions identical to those in nature or having properties similar to those of naturally-occurring phytosterols. Non-limiting suitable phytosterols include, but are not limited to, 4-desmethylsterols (e.g., 0-sitosterol, campesterol, stigmasterol, brassicasterol, 22-dehydrobrassicasterol, and A5-avenasterol), 4-monomethyl sterols, and 4,4-dimethyl sterols (triterpene alcohols) (e.g., cycloartenol, 24-methylenecycloartanol, and cyclobranol).

As used herein, the phrases "stanol", "plant stanol" and "phytostanol" are synonymous. Phytostanols are saturated sterol alcohols present in only trace amounts in nature and also may be synthetically produced, such as by hydrogenation of phytosterols. Suitable phytostanols include, but are not limited to, 0-sitostanol, campestanol, cycloartanol, and saturated forms of other triterpene alcohols.

Both phytosterols and phytostanols, as used herein, include the various isomers such as the a and p isomers. The phytosterols and phytostanols of the present invention also may be in their ester form. Suitable methods for deriving the esters of phytosterols and phytostanols are well known to those of ordinary skill in the art, and are disclosed in U.S. Pat. Nos. 6,589,588, 6,635,774, 6,800,317, and U.S. Patent Publication Number 2003/0045473. Non-limiting examples of suitable phytosterol and phytostanol esters include sitosterol acetate, sitosterol oleate, stigmasterol oleate, and their corresponding phytostanol esters. The phytosterols and phytostanols of the present invention also may include their derivatives.

The amount of functional ingredient in the beverage syrup can vary. In one embodiment, the beverage syrup comprises from about 1 ppm to about 10 wt % of a functional ingredient.

Exemplary additives include, but not limited to, carbohydrates, polyols, amino acids and their corresponding salts, poly-amino acids and their corresponding salts, sugar acids and their corresponding salts, nucleotides, organic acids, inorganic acids, organic salts including organic acid salts and organic base salts, inorganic salts, bitter compounds, caffeine, flavorants and flavoring ingredients, astringent compounds, proteins or protein hydrolysates, surfactants, emulsifiers, plant extracts, flavonoids, alcohols, polymers and combinations thereof.

In one embodiment, the composition further comprises one or more polyols. The term "polyol", as used herein, refers to a molecule that contains more than one hydroxyl group. A polyol may be a diol, triol, or a tetraol which contains 2, 3, and 4 hydroxyl groups respectively. A polyol also may contain more than 4 hydroxyl groups, such as a pentaol, hexaol, heptaol, or the like, which contain 5, 6, or 7 hydroxyl groups, respectively. Additionally, a polyol also may be a sugar alcohol, polyhydric alcohol, or polyalcohol which is a reduced form of carbohydrate, wherein the carbonyl group (aldehyde or ketone, reducing sugar) has been reduced to a primary or secondary hydroxyl group. Non-limiting examples of polyols in some embodiments include maltitol, mannitol, sorbitol, lactitol, xylitol, isomalt, propylene glycol, glycerol (glycerin), threitol, galactitol, palatinose, reduced isomalto-oligosaccharides, reduced xylo-oligosaccharides, reduced gentio-oligosaccharides, reduced maltose syrup, reduced glucose syrup, and sugar alcohols or any other carbohydrates capable of being reduced which do not adversely affect taste.

Suitable amino acid additives include, but are not limited to, aspartic acid, arginine, glycine, glutamic acid, proline, threonine, theanine, cysteine, cystine, alanine, valine, tyrosine, leucine, arabinose, trans-4-hydroxyproline, isoleucine, asparagine, serine, lysine, histidine, ornithine, methionine, carnitine, aminobutyric acid ($\alpha$-, $\beta$-, and/or $\delta$-isomers), glutamine, hydroxyproline, taurine, norvaline, sarcosine, and their salt forms such as sodium or potassium salts or acid salts. The amino acid additives also may be in the D- or L-configuration and in the mono-, di-, or tri-form of the same or different amino acids. Additionally, the amino acids may be $\alpha$-, $\beta$-, $\gamma$- and/or $\delta$-isomers if appropriate. Combinations of the foregoing amino acids and their corresponding salts (e.g., sodium, potassium, calcium, magnesium salts or other alkali or alkaline earth metal salts thereof, or acid salts) also are suitable additives in some embodiments. The amino acids may be natural or synthetic. The amino acids also may be modified. Modified amino acids refers to any amino acid wherein at least one atom has been added, removed, substituted, or combinations thereof (e.g., N-alkyl amino acid, N-acyl amino acid, or N-methyl amino acid). Non-limiting examples of modified amino acids include amino acid derivatives such as trimethyl glycine, N-methyl-glycine, and N-methyl-alanine. As used herein, modified amino acids encompass both modified and unmodified amino acids. As used herein, amino acids also encompass both peptides and polypeptides (e.g., dipeptides, tripeptides, tetrapeptides, and pentapeptides) such as glutathione and L-alanyl-L-glutamine. Suitable polyamino acid additives include poly-L-aspartic acid, poly-L-lysine (e.g., poly-L-$\alpha$-lysine or poly-L-$\epsilon$-lysine), poly-L-ornithine (e.g., poly-L-$\alpha$-ornithine or poly-L-$\epsilon$-ornithine), poly-L-arginine, other polymeric forms of amino acids, and salt forms thereof (e.g., calcium, potassium, sodium, or magnesium salts such as L-glutamic acid mono sodium salt). The poly-amino acid additives also may be in the D- or L-configuration. Additionally, the poly-amino acids may be $\alpha$-, $\beta$-, $\gamma$-, $\delta$-, and $\epsilon$-isomers if appropriate. Combinations of the foregoing poly-amino acids and their corresponding salts (e.g., sodium, potassium, calcium, magnesium salts or other alkali or alkaline earth metal salts thereof or acid salts) also are suitable additives in some embodiments. The poly-amino acids described herein also may comprise co-polymers of different amino acids. The poly-amino acids may be natural or synthetic. The poly-amino acids also may be modified, such that at least one atom has been added, removed, substituted, or combinations thereof (e.g., N-alkyl poly-amino acid or N-acyl poly-amino acid). As used herein, poly-amino acids encompass both modified and unmodified poly-amino acids. For example, modified poly-amino acids include, but are not limited to, poly-amino acids of various molecular weights (MW), such as poly-L-$\alpha$-lysine with a MW of 1,500, MW of 6,000, MW of 25,200, MW of 63,000, MW of 83,000, or MW of 300,000.

Suitable sugar acid additives include, but are not limited to, aldonic, uronic, aldaric, alginic, gluconic, glucuronic, glucaric, galactaric, galacturonic, and salts thereof (e.g., sodium, potassium, calcium, magnesium salts or other physiologically acceptable salts), and combinations thereof.

Suitable nucleotide additives include, but are not limited to, inosine monophosphate ("IMP"), guanosine monophosphate ("GMP"), adenosine monophosphate ("AMP"), cytosine monophosphate (CMP), uracil monophosphate (UMP), inosine diphosphate, guanosine diphosphate, adenosine diphosphate, cytosine diphosphate, uracil diphosphate, inosine triphosphate, guanosine triphosphate, adenosine triphosphate, cytosine triphosphate, uracil triphosphate, alkali or alkaline earth metal salts thereof, and combinations thereof. The nucleotides described herein also may comprise nucleotide-related additives, such as nucleosides or nucleic acid bases (e.g., guanine, cytosine, adenine, thymine, uracil).

Suitable organic acid additives include any compound which comprises a —COOH moiety, such as, for example, C2-C30 carboxylic acids, substituted hydroxyl C2-C30 carboxylic acids, butyric acid (ethyl esters), substituted butyric acid (ethyl esters), benzoic acid, substituted benzoic acids (e.g., 2,4-dihydroxybenzoic acid), substituted cinnamic acids, hydroxyacids, substituted hydroxybenzoic acids, anisic acid substituted cyclohexyl carboxylic acids, tannic acid, aconitic acid, lactic acid, tartaric acid, citric acid, isocitric acid, gluconic acid, glucoheptonic acids, adipic acid, hydroxycitric acid, malic acid, fruitaric acid (a blend of malic, fumaric, and tartaric acids), fumaric acid, maleic acid, succinic acid, chlorogenic acid, salicylic acid, creatine, caffeic acid, bile acids, acetic acid, ascorbic acid, alginic acid, erythorbic acid, polyglutamic acid, glucono delta lactone, and their alkali or alkaline earth metal salt derivatives thereof. In addition, the organic acid additives also may be in either the D- or L-configuration.

Suitable organic acid additive salts include, but are not limited to, sodium, calcium, potassium, and magnesium salts of all organic acids, such as salts of citric acid, malic acid, tartaric acid, fumaric acid, lactic acid (e.g., sodium lactate), alginic acid (e.g., sodium alginate), ascorbic acid (e.g., sodium ascorbate), benzoic acid (e.g., sodium benzoate or potassium benzoate), sorbic acid and adipic acid. The examples of the organic acid additives described optionally may be substituted with at least one group chosen from hydrogen, alkyl, alkenyl, alkynyl, halo, haloalkyl, carboxyl, acyl, acyloxy, amino, amido, carboxyl derivatives, alkylamino, dialkylamino, arylamino, alkoxy, aryloxy, nitro, cyano, sulfo, thiol, imine, sulfonyl, sulfenyl, sulfinyl, sulfamyl, carboxalkoxy, carboxamido, phosphonyl, phosphinyl, phosphoryl, phosphino, thioester, thioether, anhydride, oximino, hydrazino, carbamyl, phosphor or phosphonato. In particular embodiments, the organic acid additive is present in the sweetener composition in an amount effective to provide a concentration from about 10 ppm to about 5,000 ppm when present in a consumable, such as, for example, a beverage.

Suitable inorganic acid additives include, but are not limited to, phosphoric acid, phosphorous acid, polyphosphoric acid, hydrochloric acid, sulfuric acid, carbonic acid, sodium dihydrogen phosphate, and alkali or alkaline earth metal salts thereof (e.g., inositol hexaphosphate Mg/Ca).

Suitable bitter compound additives include, but are not limited to, caffeine, quinine, urea, bitter orange oil, naringin, quassia, and salts thereof.

Suitable flavorants and flavoring ingredient additives include, but are not limited to, vanillin, vanilla extract, mango extract, cinnamon, citrus, coconut, ginger, viridiflorol, almond, menthol (including menthol without mint), grape skin extract, and grape seed extract. "Flavorant" and "flavoring ingredient" are synonymous and can include natural or synthetic substances or combinations thereof. Flavorants also include any other substance which imparts flavor and may include natural or non-natural (synthetic) substances which are safe for human or animals when used in a generally accepted range. Non-limiting examples of proprietary flavorants include Dohler™ Natural Flavoring Sweetness Enhancer K14323 (Dohler™ Darmstadt, Germany), Symrise™ Natural Flavor Mask for Sweeteners 161453 and 164126 (Symrise™, Holzminden, Germany), Natural Advantage™ Bitterness Blockers 1, 2, 9 and 10 (Natural Advantage™, Freehold, New Jersey, U.S.A.), and Sucramask™ (Creative Research Management, Stockton, California, U.S.A.).

Suitable polymer additives include, but are not limited to, chitosan, pectin, pectic, pectinic, polyuronic, polygalacturonic acid, starch, food hydrocolloid or crude extracts thereof (e.g., gum acacia senegal (Fibergum™), gum acacia seyal, carageenan), poly-L-lysine (e.g., poly-L-α-lysine or poly-L-ε-lysine), poly-L-ornithine (e.g., poly-L-α-ornithine or poly-L-ε-ornithine), polypropylene glycol, polyethylene glycol, poly(ethylene glycol methyl ether), polyarginine, polyaspartic acid, polyglutamic acid, polyethylene imine, alginic acid, sodium alginate, propylene glycol alginate, and sodium polyethyleneglycolalginate, sodium hexametaphosphate and its salts, and other cationic polymers and anionic polymers.

Suitable protein or protein hydrolysate additives include, but are not limited to, bovine serum albumin (BSA), whey protein (including fractions or concentrates thereof such as 90% instant whey protein isolate, 34% whey protein, 50% hydrolyzed whey protein, and 80% whey protein concentrate), soluble rice protein, soy protein, protein isolates, protein hydrolysates, reaction products of protein hydrolysates, glycoproteins, and/or proteoglycans containing amino acids (e.g., glycine, alanine, serine, threonine, asparagine, glutamine, arginine, valine, isoleucine, leucine, norvaline, methionine, proline, tyrosine, hydroxyproline, and the like), collagen (e.g., gelatin), partially hydrolyzed collagen (e.g., hydrolyzed fish collagen), and collagen hydrolysates (e.g., porcine collagen hydrolysate).

Suitable surfactant additives include, but are not limited to, polysorbates (e.g., polyoxyethylene sorbitan monooleate (polysorbate 80), polysorbate 20, polysorbate 60), sodium dodecylbenzenesulfonate, dioctyl sulfosuccinate or dioctyl sulfosuccinate sodium, sodium dodecyl sulfate, cetylpyridinium chloride (hexadecylpyridinium chloride), hexadecyltrimethylammonium bromide, sodium cholate, carbamoyl, choline chloride, sodium glycocholate, sodium taurodeoxycholate, lauric arginate, sodium stearoyl lactylate, sodium taurocholate, lecithins, sucrose oleate esters, sucrose stearate esters, sucrose palmitate esters, sucrose laurate esters, and other emulsifiers, and the like.

Suitable flavonoid additives are classified as flavonols, flavones, flavanones, flavan-3-ols, isoflavones, or anthocyanidins. Non-limiting examples of flavonoid additives include, but are not limited to, catechins (e.g., green tea extracts such as Polyphenon™ 60, Polyphenon™ 30, and Polyphenon™ 25 (Mitsui Norin Co., Ltd., Japan), polyphenols, rutins (e.g., enzyme modified rutin Sanmelin™ AO (San-fi Gen F.F.I., Inc., Osaka, Japan)), neohesperidin, naringin, neohesperidin dihydrochalcone, and the like.

Suitable alcohol additives include, but are not limited to, ethanol.

Suitable astringent compound additives include, but are not limited to, tannic acid, europium chloride ($EuCl_3$), gadolinium chloride ($GdCl_3$), terbium chloride ($TbCl_3$), alum, tannic acid, and polyphenols (e.g., tea polyphenols).

The amount of additive in the beverage syrup can vary. In one embodiment, the beverage syrup comprises from about 1 ppm to about 10 wt % of an additive.

The pH of the beverage syrup is typically from about 2.0 to about 5, such as, for example, from about 2.5 to about 4. The pH may be adjusted by addition of a suitable acid or base such as, but not limited to phosphoric acid, citric acid, or sodium hydroxide.

The resulting beverage syrup is packaged and may be stored. A beverage syrup may be used essentially immediately to manufacture beverages, which typically are packaged for distribution. A beverage syrup also may be distributed to bottlers, who package beverages made by addition of water and optionally other materials, e.g. carbonation.

The beverage syrup can be a full-calorie beverage syrup such that a ready-to-drink beverage prepared from the beverage syrup has up to about 120 calories per 8 oz serving.

The beverage syrup can be a mid-calorie beverage syrup, such that a ready-to-drink beverage prepared from the beverage syrup has up to about 60 calories per 8 oz. serving.

The beverage syrup can be a low-calorie beverage syrup, such that a ready-to-drink beverage prepared from the beverage syrup has up to about 40 calories per 8 oz. serving.

The beverage syrup can be a zero-calorie beverage syrup, such that a ready-to-drink beverage prepared from the beverage syrup has less than about 5 calories per 8 oz. serving.

IV. Beverages and Method of Making Same

The present invention also provides ready-to-drink beverages prepared from the beverage syrups described herein and methods of preparing ready-to-drink beverages.

Ready-to-drink beverages include carbonated and non-carbonated beverages. Carbonated beverages include, but are not limited to, frozen carbonated beverages, enhanced sparkling beverages, cola, fruit-flavored sparkling beverages (e.g. lemon-lime, orange, grape, strawberry and pineapple), ginger-ale, soft drinks and root beer. Non-carbonated beverages include, but are not limited to, fruit juice, fruit-flavored juice, juice drinks, nectars, vegetable juice, vegetable-flavored juice, sports drinks, energy drinks, enhanced water drinks, enhanced water with vitamins, near water drinks (e.g., water with natural or synthetic flavorants), coconut water, tea type drinks (e.g. black tea, green tea, red tea, oolong tea), coffee, cocoa drink, beverage containing milk components (e.g. milk beverages, coffee containing milk components, café au lait, milk tea, fruit milk beverages), beverages containing cereal extracts and smoothies.

A method of preparing a beverage comprises mixing a beverage syrup described herein with an appropriate quantity of diluting water.

Typically, the volumetric ratio of syrup to water is between 1:3 to 1:8, such as, for example, between 1:3 and 1:8, between 1:3 and 1:7, between 1:3 and 1:6, between 1:3 and 1:5, between 1:3 and 1:4, between 1:4 and 1:8, between 1:4 and 1:7, between 1:4 and 1:6, between 1:4 and 1:5, between 1:5 and 1:8, between 1:5 and 1:7, between 1:5 and 1:6, between 1:6 and 1:8, between 1:6 and 1:7 and between 1:7 and 1:8.

The temperature at which the mixing is done is preferably under about 70° C. to minimize degradation of steviol glycosides.

In one embodiment, the beverage is a carbonated beverage (e.g. fountain drink or soft drink) and the diluting water is carbonated water. The beverage is typically dispensed for immediate consumption.

Other types of water typical in beverage manufacturing and be used to prepare beverages, e.g. deionized water, distilled water, reverse osmosis water, carbon-treated water, purified water, demineralized water and combinations thereof.

The beverage can be a full-calorie beverage that has up to about 120 calories per 8 oz serving.

The beverage can be a mid-calorie beverage that has up to about 60 calories per 8 oz. serving.

The beverage can be a low-calorie beverage that has up to about 40 calories per 8 oz. serving.

The beverage can be a zero-calorie that has less than about 5 calories per 8 oz. serving.

EXAMPLES

In the following examples, "RebM80" refers to a steviol glycoside mixture containing at least 80% Reb M by weight (the majority of the remainder is Reb D and Reb A). "RebM95" refers to a steviol glycoside mixture containing at least 95% Reb M by weight. The total steviol glycoside content of the mixtures is at least 95%. Methods of purifying Reb M to the appropriate purity levels are known to those of skill in the art, e.g. the method described in WO2013/096420.

Example 1

Citrate buffer was prepared using trisodium citrate and citric acid and ultrapurified water to give pH 3 to pH 3.2 and 0.1 molar concentration. The mass of RebM95 in Table 1 was added to the mass of citrate buffer listed in Table 1, and to that the mass of surfactant listed in Table 1 was added. The mixture was applied to a vortex mixture at 3000 rpm for 20 seconds and applied to a 45° C. water bath for 10 minutes. Samples A1 to A6 refer to SDS (sodium dodecyl sulfate) as the surfactant and B1-B6 as CTAB (cetyl trimethylammonium bromide) as the surfactant.

TABLE 1

| Sample | Mass RebM | Mass Citrate | Mass Surfactant | wt % RebM | wt % Surf | Mol Ratio | Surf Conc mM | Above CMC | Appearance after 45 C. |
|---|---|---|---|---|---|---|---|---|---|
| A1 | 0.1014 | 14.9264 | 0 | 0.67 | 0 | | 0 | no | much precip |
| A2 | 0.1014 | 14.9232 | 0.0015 | 0.67 | 0.0099 | 15.1 | 0.35 | no | much precip |
| A3 | 0.1016 | 14.9021 | 0.0042 | 0.68 | 0.0279 | 5.40 | 0.98 | no | precip |
| A4 | 0.1038 | 14.9145 | 0.0088 | 0.69 | 0.0585 | 2.63 | 2.0 | no | precip |
| A5 | 0.1005 | 14.9119 | 0.0149 | 0.67 | 0.0991 | 1.51 | 3.46 | no | little precip |
| A6 | 0.1013 | 14.9067 | 0.0226 | 0.67 | 0.1503 | 1.00 | 5.26 | no | Clear |
| B1 | 0.1007 | 15.0277 | 0 | 0.67 | 0 | | 0 | no | much precip |
| B2 | 0.101 | 14.9019 | 0.0015 | 0.67 | 0.0099 | 19.0 | 0.28 | no | much precip |
| B3 | 0.1006 | 14.9035 | 0.0044 | 0.67 | 0.0293 | 6.45 | 0.81 | no | precip |
| B4 | 0.1014 | 14.9137 | 0.0086 | 0.67 | 0.0572 | 3.33 | 1.6 | yes | little precip |
| B5 | 0.1011 | 14.9103 | 0.0148 | 0.67 | 0.0984 | 1.93 | 2.7 | yes | little precip |
| B6 | 0.1001 | 14.9104 | 0.022 | 0.67 | 0.1463 | 1.28 | 4.0 | yes | Clear |

The RebM95 content was measured by HPLC. The results are shown in Tables 2 and 3.

TABLE 2

| Sample | Measured RebM95 content by HPLC (ppm) | Measured RebM95 Content by HPLC (wt %) |
|---|---|---|
| A1 | 1509.780032 | 0.150978003 |
| A2 | 1469.689673 | 0.146968967 |
| A3 | 1662.182355 | 0.166218236 |
| A4 | 2405.033134 | 0.240503313 |
| A5 | 2971.604245 | 0.297160424 |
| A6 | 5559.790691 | 0.555979069 |

TABLE 3

| Sample | Measured RebM95 content by HPLC (ppm) | Measured RebM95 Content by HPLC (wt %) |
|---|---|---|
| B1 | 1458.782737 | 0.145878274 |
| B2 | 1549.280828 | 0.154928083 |
| B3 | 1877.078473 | 0.187707847 |
| B4 | 2301.564633 | 0.230156463 |
| B5 | 2711.31169 | 0.271131169 |
| B6 | 5526.480318 | 0.552648032 |

Example 2

RebM95 of the specified mass and SDS of the specified mass were combined with water as needed to bring to approximately 8.3 to 8.45 grams at 3 wt % RebM95 loading. The mixtures were mixed with a vortex mixer at 3000 rpm for 20 seconds and then heated to 60° C. for 10 minutes. Visual clarity as a measure of solubility was noted.

TABLE 4

| Sample | Total mass | wt % RebM95 | wt % SDS | Wt Ratio RebM95/SDS | soluble at RT | soluble with heat | Above CMC* |
|---|---|---|---|---|---|---|---|
| A | 8.37 | 3.02 | 0 | | No | No | No |
| B | 8.34 | 3.04 | 0.68 | 4.49 | No | Yes | Yes |
| C | 8.32 | 3.05 | 1.34 | 2.28 | Yes | Yes | Yes |
| D | 8.33 | 3.03 | 2.00 | 1.52 | Yes | Yes | Yes |
| E | 8.41 | 3.00 | 0.13 | 23.58 | No | | No |
| F | 8.42 | 3.01 | 0.25 | 11.90 | No | | Yes |

*critical micelle concentration

Example 3

The solubility of samples containing RebM95 and non-ionic surfactants were evaluated.

Samples having the RebM wt % s indicated in Table 5 were prepared in water. In samples A, C and D, the non-ionic surfactant was Q-Naturale (a saponin). The mixture was mixed with a vortex mixer at 3000 rpm for 20 seconds and applied to a 45° C. water bath for 10 minutes. In samples E and F, the non-ionic surfactant was a Sucrose Fatty Acid Ester (SFAE). Sample B was the control with no surfactant present. Solubility was measured using HPLC. It was found that the non-ionic surfactants showed no solubilizing power in this range.

TABLE 5

| Sample | RebM (wt %) | Surfactant (wt %) | Corrected | Measured |
|---|---|---|---|---|
| A | 0.36 | 0.102 | 0.0153 | 0.2886 |
| B | 0.362 | 0 | 0 | 0.3074 |
| C | 0.357 | 0.305 | 0.04575 | 0.2971 |
| D | 0.357 | 0.626 | 0.0939 | 0.29 |
| E | 0.345 | 0.0277 | 0.0277 | 0.2919 |
| F | 0.346 | 0.05 | 0.05 | 0.2951 |

The invention claimed is:

1. A method of preparing a concentrated solution having at least about 2 wt % rebaudioside M content comprising:
   a. combining (i) a crystalline steviol glycoside composition comprising rebaudioside M, (ii) at least one surfactant selected from a cationic surfactant and an anionic surfactant, and (iii) an aqueous solution to provide a mixture;
   b. heating the mixture to provide a clear solution; and
   c. cooling the clear solution to about room temperature to provide a concentrate;
   wherein the weight ratio of the crystalline steviol glycoside composition comprising rebaudioside M to the at least one surfactant is about 5:1 to about 1:1.

2. The method of claim 1, wherein the crystalline steviol glycoside composition comprises at least about 80% rebaudioside M by weight and has a total steviol glycoside content of about 95% by weight.

3. The method of claim 2, wherein the crystalline steviol glycoside composition comprises at least about 95% rebaudioside M by weight and has a total steviol glycoside content of about 95% by weight.

4. The method of claim 1, wherein the at least one surfactant is a cationic surfactant selected from the group consisting of octenidine dihydrochloride, cetyl trimethylammonium bromide (CTAB), cetylpyridinium chloride, benzalkonium chloride, benzethonium chloride, 5-bromo-5-nitro-1,3-dioxane, dimethyldioctadecylammonium chloride, choline chloride, cetrimonium bromide, hexadecyltrimethylammonium bromide, dioctdecyldimethylammonium bromide and combinations thereof.

5. The method of claim 1, wherein the at least one surfactant is an anionic surfactant selected from the group consisting of ammonium laurel sulfate, sodium dodecylbenzenesulfonate, sodium dodecyl sulfate, sodium laureth sulfate (SLS), sodium myreth sulfate, dioctyl sodium sulfosuccinate (DOSS), perfluorooctanesulfonate (PFOS), perfluorobutanesulfonate, linear alkyl benzene sulfonates, sodium dodecyl sulfate (SDS), sodium stearate, sodium cholate, sodium glycocholate, sodium taurodeoxycholate, sodium stearoyl lactylate and combinations thereof.

6. The method of claim 1, wherein the aqueous solution is water or an aqueous buffer.

7. The method of claim 1, wherein the concentrate is clear by visual inspection for at least about 72 hours after preparation.

8. A method of making a beverage syrup comprising combining a concentrate according to claim 1 with a compound selected from the group consisting of additional sweeteners, functional ingredients, additives and combinations thereof.

9. The method of claim 1, further comprising combining the concentrate with at least one compound selected from the group consisting of additional sweeteners, functional ingredients, additives and combinations thereof, thereby providing a beverage syrup.

10. The method of claim 9, further comprising mixing the beverage syrup with a quantity of diluting water, thereby providing a beverage, wherein
   the volumetric ratio of syrup to water is between about 1:3 to about 1:8.

11. The method of claim 10, wherein the beverage is a carbonated beverage and the diluting water is carbonated water.

12. The method of claim 10, wherein the beverage is selected from the group consisting of a zero-calorie beverage, a low-calorie beverage and a mid-calorie beverage.

13. The method of claim 10, wherein the beverage is selected from the group consisting of enhanced sparkling beverages, cola, fruit-flavored sparkling beverages, ginger-ale, soft drinks and root beer.

14. The method of claim 1, wherein the concentrated solution has at least about 3 wt % rebaudioside M content.

15. The method of claim 1, wherein the crystalline steviol glycoside composition comprising rebaudioside M comprises at least about 80% rebaudioside M by weight.

16. The method of claim 8, wherein the beverage syrup comprises one or more additional sweeteners selected from the group consisting of: siamenoside, monatin and its salts, curculin, mogrosides, glycyrrhizic acid and its salts, thaumatin, monellin, mabinlin, brazzein, hernandulcin, phyllodulcin, glycyphyllin, phloridzin, trilobatin, baiyunoside, osladin, polypodoside A, pterocaryoside A, pterocaryoside B, mukurozioside, phlomisoside I, periandrin I, abrusoside A, steviolbioside and cyclocarioside I, sugar alcohols such as erythritol, sucralose, potassium acesulfame, acesulfame acid and salts thereof, aspartame, alitame, saccharin and salts thereof, neohesperidin dihydrochalcone, cyclamate, cyclamic acid and salts thereof, neotame, advantame, glucosylated steviol glycosides and combinations thereof.

17. The method of claim 8, wherein the beverage syrup comprises one or more functional ingredients selected from the group consisting of: organic acid salts.

* * * * *